(12) United States Patent
Jahns et al.

(10) Patent No.: US 8,052,593 B2
(45) Date of Patent: Nov. 8, 2011

(54) IMPLANTABLE MALLEABLE PENILE PROSTHETIC DEVICE

(75) Inventors: Scott E. Jahns, Hudson, WI (US); Russell Robert Paul, Brooklyn Park, MN (US); Shiva Prakash Moosai, New Hope, MN (US)

(73) Assignee: AMS Research Corporation, Minnetonka, MN (US)

( * ) Notice: Subject to any disclaimer, the term of this patent is extended or adjusted under 35 U.S.C. 154(b) by 1049 days.

(21) Appl. No.: 11/923,171

(22) Filed: Oct. 24, 2007

(65) Prior Publication Data
US 2008/0103353 A1     May 1, 2008

Related U.S. Application Data

(60) Provisional application No. 60/862,653, filed on Oct. 24, 2006.

(51) Int. Cl.
*A61F 5/00* (2006.01)
(52) U.S. Cl. .......................................... 600/40
(58) Field of Classification Search ............... 600/38–41
See application file for complete search history.

(56) References Cited

U.S. PATENT DOCUMENTS

| | | |
|---|---|---|
| 3,832,996 A | 9/1974 | Kalnberz |
| 3,893,456 A | 7/1975 | Small et al. |
| 3,987,789 A | 10/1976 | Timm et al. |
| 3,991,752 A | 11/1976 | Gerow |
| 4,066,073 A | 1/1978 | Finney et al. |
| 4,151,840 A | 5/1979 | Barrington |
| 4,177,805 A | 12/1979 | Tudoriu |
| 4,187,839 A | 2/1980 | Nuwayser et al. |
| 4,204,530 A | 5/1980 | Finney |
| 4,244,370 A | 1/1981 | Furlow et al. |
| 4,345,339 A | 8/1982 | Muller et al. |
| 4,353,360 A | 10/1982 | Finney et al. |
| 4,392,562 A | 7/1983 | Burton et al. |
| 4,411,260 A | 10/1983 | Koss |
| 4,411,261 A | 10/1983 | Finney |
| 4,483,331 A | 11/1984 | Trick |
| 4,517,967 A | 5/1985 | Timm et al. |
| 4,522,198 A | 6/1985 | Timm et al. |

(Continued)

FOREIGN PATENT DOCUMENTS

EP    0137752 B1    8/1989

(Continued)

OTHER PUBLICATIONS

Acu-Form Penile Prosthesis, Mentor, 1 page Aug. 1997.

(Continued)

*Primary Examiner* — John Lacyk
(74) *Attorney, Agent, or Firm* — Westman, Champlin & Kelly, P.A.

(57) ABSTRACT

A prosthetic device comprises stacked column segments. A first one of the column segments comprises a ball surface facing along a column axis. The ball surface has a generally convex shape that is articulable in a mating socket of a second one of the column segments. The first one of the column segments comprises a socket surface facing an opposite direction along the column axis. The socket surface has a generally concave shape that is articulable on a mating ball of a third one of the column segments. Multiple column segments similar to the first column segment are stacked to form the column.

15 Claims, 16 Drawing Sheets

U.S. PATENT DOCUMENTS

| | | | |
|---|---|---|---|
| 4,541,420 | A | 9/1985 | Timm et al. |
| 4,545,081 | A | 10/1985 | Nestor et al. |
| 4,594,998 | A | 6/1986 | Porter et al. |
| 4,619,251 | A | 10/1986 | Helms et al. |
| 4,665,902 | A | 5/1987 | Goff et al. |
| 4,666,428 | A | 5/1987 | Mattioli et al. |
| 4,669,456 | A | 6/1987 | Masters |
| 4,693,719 | A | 9/1987 | Franko et al. |
| 4,699,128 | A | 10/1987 | Hemmeter |
| 4,807,608 | A | 2/1989 | Levius |
| 4,881,531 | A | 11/1989 | Timm et al. |
| 4,899,737 | A | 2/1990 | Lazarian |
| 4,988,357 | A | 1/1991 | Koss |
| 5,050,592 | A | 9/1991 | Olmedo |
| 5,176,708 | A | 1/1993 | Frey et al. |
| 5,283,390 | A | 2/1994 | Hubis et al. |
| 5,445,594 | A | 8/1995 | Elist |
| 5,468,213 | A * | 11/1995 | Polyak .......................... 600/40 |
| 5,509,891 | A | 4/1996 | DeRidder |
| 5,512,033 | A | 4/1996 | Westrum, Jr. et al. |
| 5,553,379 | A | 9/1996 | Westrum, Jr. et al. |
| 6,579,230 | B2 | 6/2003 | Yachia et al. |
| 6,600,108 | B1 | 7/2003 | Mydur et al. |
| 2005/0014993 | A1 | 1/2005 | Mische |

FOREIGN PATENT DOCUMENTS

| | | |
|---|---|---|
| EP | 0774935 B1 | 11/1999 |
| GB | 2151484 A | 7/1985 |
| WO | WO8601398 A1 | 3/1986 |
| WO | WO9604865 A1 | 2/1996 |

OTHER PUBLICATIONS

Agrawal, Wineet, et al., An Audit of Implanted Penile Prostheses in the UK, BJU International pp. 393-395 (2006).

Akand, Murat Mechanical Failure With Malleable Penile Prosthesis, J. Urol. 70: 1007.e11-1007.e12 (2007).

AMS Malleable 600.TM. American Medical Systems Publication 30915, 1983.

Anafarta, Kadri, Clinical Experience With Inflatable and Malleable Penile Implants in 104 Patients, Urol. Int. 56: 100-104 (1996).

Benson RC Jr, Patterson DE, Barrett DM. Long-term results with the Jonas malleable penile prosthesis. J Urol. Nov. 1985;134(5):899-901.

Burns-Cox, N., Fifteen Years Experience of Penile Prosthesis Insertion, International J. Impotence Res. (1997) 9, 211-216.

Chiang, Han-Sun, 10 Years of Experience With Penile Prosthesis Implantation in Taiwanese Patients, J. Urol. vol. 163: 476-480(2000).

Choi, Hyung Ki, Ten Years of Experience With Various Penile Prosthesis in Korean, Yasel Medical J. Wol. 35, No. 2, (1994) 209-217.

Dorfinger T, Bruskewitz R. AMS malleable penile prosthesis. Urology. Dec. 1986;28(6):480-5.

Fathey, Ahmad, Experience With Tube (PROMEDON_Malleable Penile Implant, Urol. Int. 2007; 79:244-247.

Ferguson, Kenneth, Prospective Long-Term Results and Ouality-of-Life-Assessment After Dura-II Penile Prosthesis Placement, Urol. 61(2) 437-441 (2003).

Fogarty, JD, Cutaneous Temperature Measurements in Men With Penile Prostheses: A Comparison Study, Int. J. of Impotence Res. (2005) 17, 506-509.

Henry, Gerard D., Advances in Penile Prosthesis Design, Curr Sex Health report 2007;4:15-19.

Jonas U. [Silicone-silver penis prosthesis (Jonas-Eska), long-term reconstruction. J Urol. Sep. 1998;160(3 Pt 2):1164-8.

Kardar, A.H., An Unusual Complication of Penile Prosthesis Following Urethroplasty, Scand. J. Urol. Nephrol. 36: 89-90, 2002.

Kaufman JJ, Raz S. Use of implantable prostheses for the treatment of urinary incontinence and impotence. Am J Surg. Aug. 1975;130(2):244-50.

Khoudary, Kevin, Design Considerations in Penile Prostheses: The American Medical Systems Product Line, J. Long-Term Effects of Medical Implants, 7(1):55-64 (1997).

Krauss, Dennis J., Use of the Malleable Penile Prosthesis in the Treatment of Erectile Dysfunction: A Prospective Study of Postoperative . . . , J. Urol. vol. 142: 988-991(1989).

Lazarou, Stephen, Technical Advances in Penile Prostheses, J. Long-Term effects of Medical Implants, 16(3):235-247 (2006).

Maul Judd, Experience With the AMS 600 Malleable Penile Prosthesis, J Urol. 135:929-931 (1986).

Mentor Urology Products, 18 pages (May 1998).

Merino, G. Atienza, Penile Prosthesis for the Treatment of Erectile Dysfunction, Actas Urol. Esp. 2006: 30 (2): 159-169.

Minervini, Andrea, Outcome of Penile Prosthesis Implantation for Treating Erectile Dysfunction: Experience With 504 Procedures, BJU International 97:129-133, (2005).

Montague, Drogo, Clinical Guidelines Panel on Erectile Dysfunction: Summary Report on the Treatment of Organic Erectile Dysfunction, J. Urol. 156:2007-2011 (1996).

Montague, Drogo, Contemporary Aspects of Penile Prosthesis Implantation, urol Int 2003: 70: 141-146.

Montague, Drogo, Current Status of Penile Prosthesis Implantation, Urology Reports 2000, 1: 291-296.

Montague, Drogo, Experience With Semirigid Rod and Inflatable Penile Prostheses, J. Urol. 129:967-968, 1983.

Montague, Drogo, Penile Prosthesis Implantation, 712-719 1994.

Montague, Drogo, Penile Prosthesis Implantation for End-Stage Erectile Dysfunction After Radical Prostatectomy, Reviews in Urol. vol. 7 Suppl. 2 S51-S57 2005.

Montague, Drogo, Surgical Approaches for Penile Prostheses Implantation: Penoscrotal vs Infrapubic, International J. Impotence Res. (2003) 15, Suppl. 5 , S134-S135.

Morey, Allen, et al, Immediate Insertion of a Semirigid Penile Prosthesis for Refractory Ischemic Priapism, Military Medicine, 172, 11:1211, 2007.

Mulcahy, John, Another Look At the Role of Penile Prostheses in the Management of Impotence, Urology Annual 11, pp. 169-185 (1997).

Paula, B. G. Revision Surgery for Penile Implants, Int. J. Impotence res. (1994) 6, 17-23.

Pearman RO. Insertion of a silastic penile prosthesis for the treatment of organic sexual impotence. J Urol. May 1972;107(5):802-6.

Randrup, Eduardo, Penile Implant Surgery: Rear Tip Extender That Stays Behind, Urology 1992 34,1 p. 87.

Rhee, Eugene, Technique for Concomitant Implantation of the Penile Prosthesis With the Male Sling, J. Urol. 173: 925-927 (2006).

Salama, Nadar, Satisfaction With the Malleable Penile Prosthesis Among Couples From the Middle East: Is It Different . . . , Int. J. Impotence Res. 16:175-180 (2004).

Small, Michael, Small-Carrion Penile Prosthesis: A Report on 160 Cases and Review of the Literature, J. Urol. vol. 167, 2357-2360, Jun. 2002.

Smith, Christopher, Management of Impending Penile Prosthesis Erosion With a Polytetrafluoroethylene Distal Wind Sock Graft, J. Urol. vol. 160: 2037-2040, (1998).

Stein, Avi et al., Malleable Penile Prosthesis Removal Leaving Behind the Rear Tip Extenders: A Clinical Presentation, Urol. Int. 50:119-120 (1993).

Surgical Protocol, Mentor 5 pages Sep. 1997.

The AMS Hydroflex Self-Contained Penile Prosthesis, American Medical Systems Publication 50513 (1985).

Yoo JJ, Lee I, Atala A. Cartilage rods as a potential material for penile reconstruction. J Urol. Sep. 1998;160(3 Pt 2):1164-8; discussion 1178.

Zerman, Dirk-Henrik, et al. Penile Prosthetic Surgery in Neurologically Impaired Patients: Long-Term Follow-Up, J Urol 175: 1041-1044. (2006).

* cited by examiner

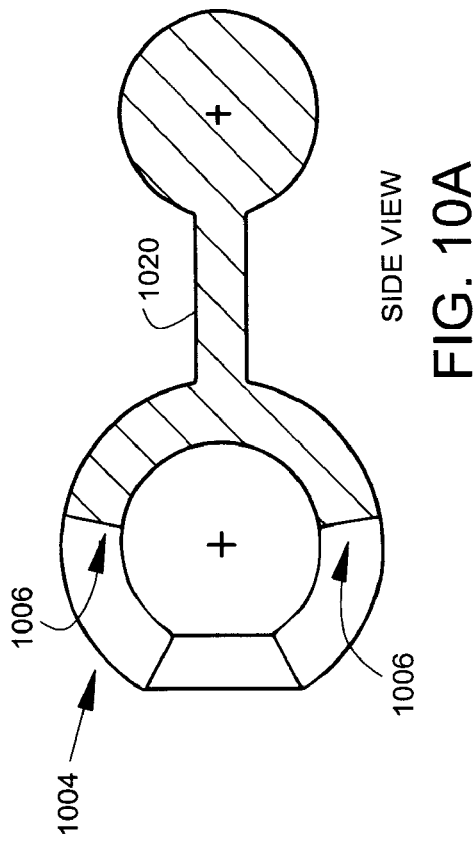
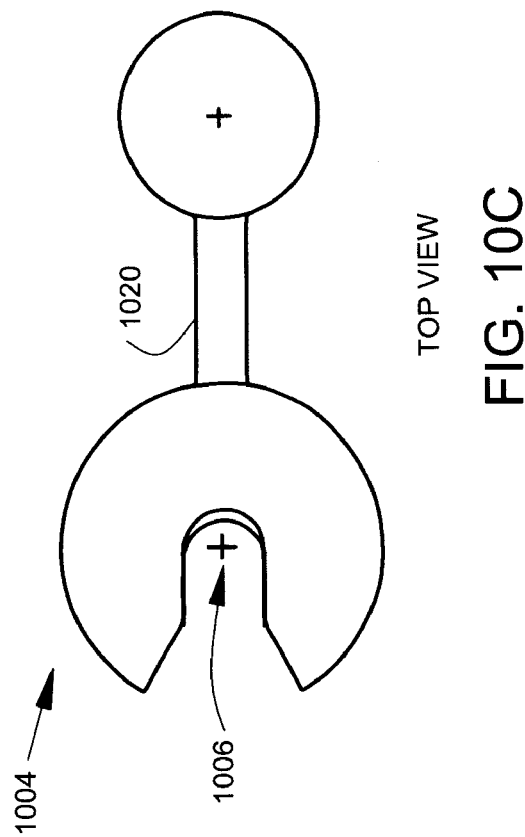
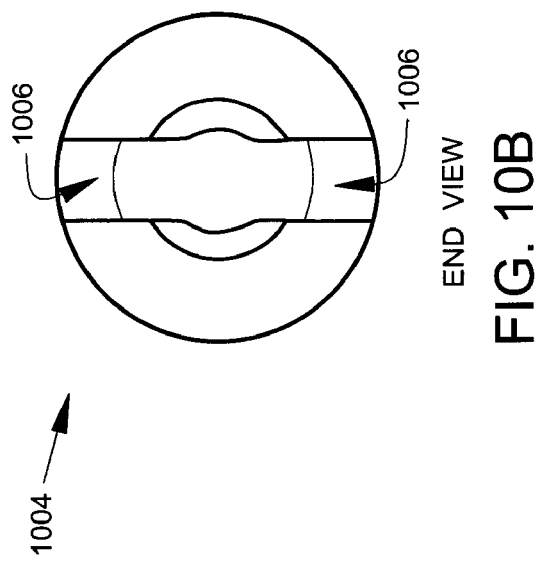
FIG. 10A SIDE VIEW
FIG. 10B END VIEW
FIG. 10C TOP VIEW

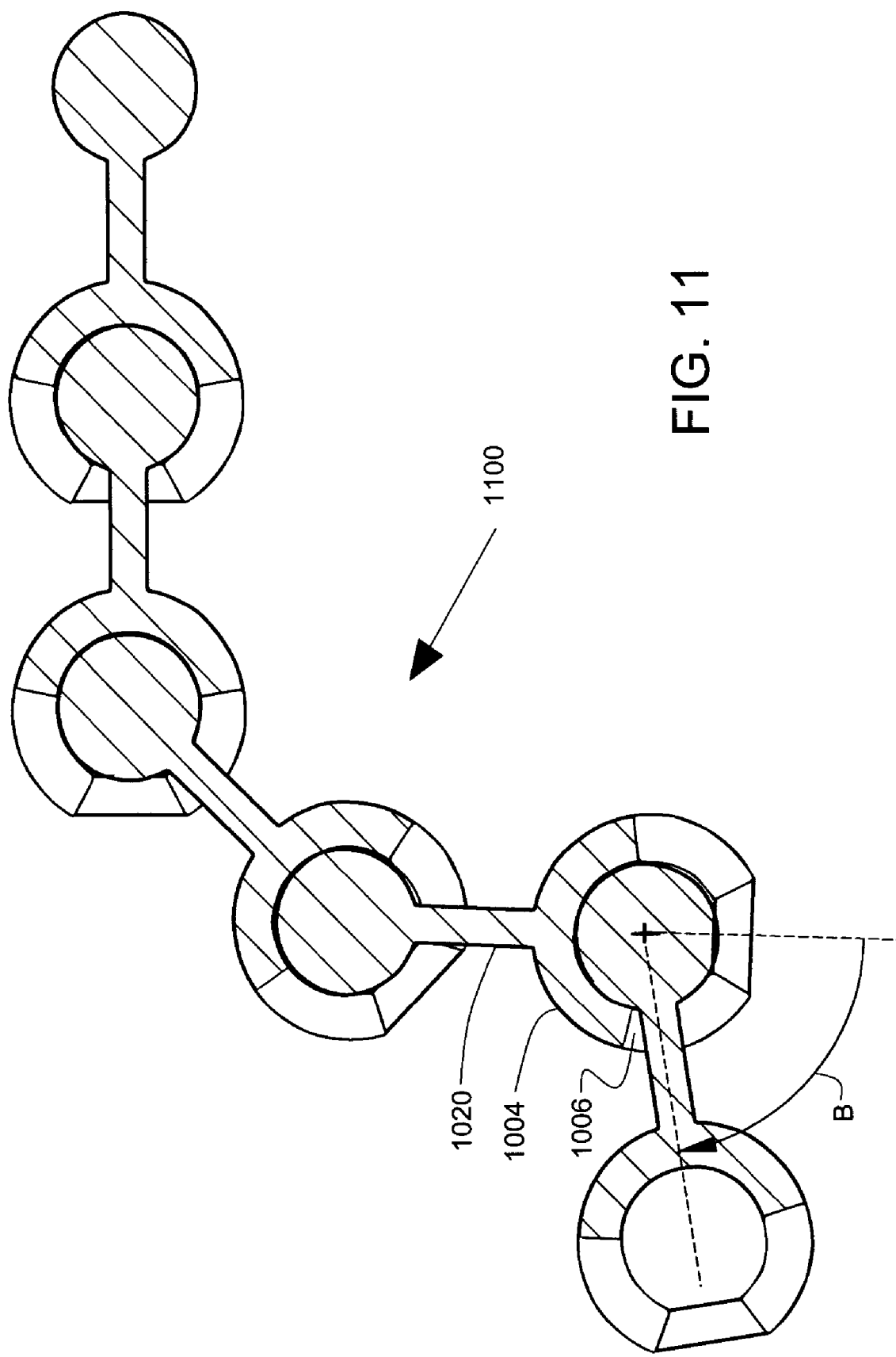

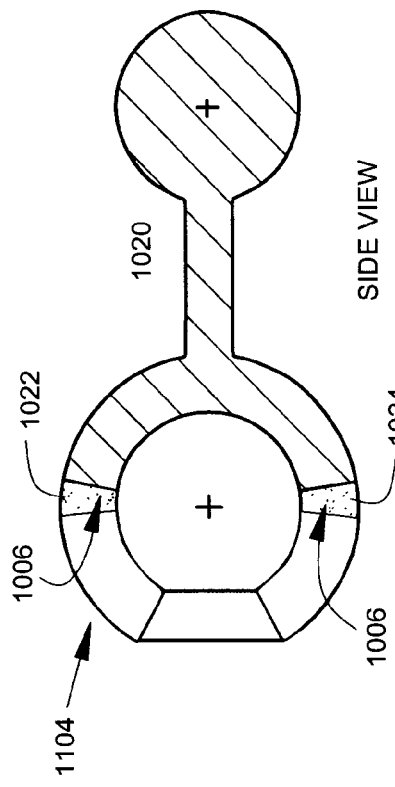
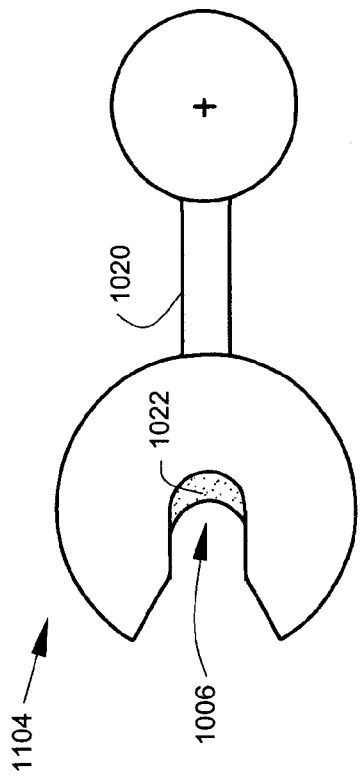
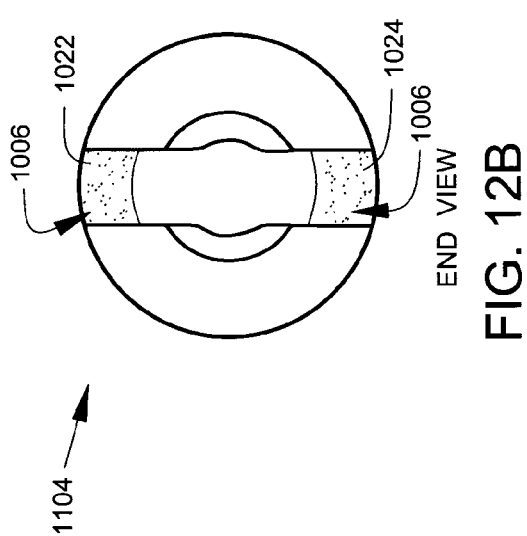
FIG. 12A SIDE VIEW
FIG. 12B END VIEW
FIG. 12C TOP VIEW

IMPLANTABLE MALLEABLE PENILE PROSTHETIC DEVICE

The present application claims the benefit of U.S. Provisional Patent Application Ser. No. 60/862,653, filed Oct. 24, 2006.

FIELD OF THE INVENTION

This invention relates to implantable prostheses. In particular, but not by way of limitation, this invention relates to implantable malleable penile prostheses.

BACKGROUND

Various types of penile prostheses are currently available to cure or compensate for impotence, two of which include a non-inflatable, semi-rigid implantable prostheses and an inflatable, implantable prostheses. The non-inflatable, semi-rigid prosthesis is implanted within the corpora cavernosa of the penis and provides a generally constant erection. The inflatable prosthesis is also implanted in the corpora cavernosa but is connected to a hydraulic pumping device.

There is a continuous demand for improvements to implantable non-inflatable penile prostheses including, for example, easier construction, improved articulation, quieter articulation and other improvements.

Embodiments of the present invention provide solutions to these and other problems. The discussion above is merely provided for general background information and is not intended to be used as an aid in determining the scope of the claimed subject matter.

SUMMARY OF THE INVENTION

Disclosed is an implantable malleable penile prosthetic device comprising stacked column segments. A first one of the column segments comprises a ball surface facing along a column axis. The ball surface has a generally convex shape that is articulable in a mating socket of a second one of the column segments. The first one of the column segments comprises a socket surface facing an opposite direction along the column axis. The socket surface has a generally concave shape that is articulable on a mating ball of a third one of the column segments. Multiple column segments similar to the first column segment are stacked to form the column.

BRIEF DESCRIPTION OF THE DRAWINGS

FIG. 10 illustrates an embodiment of a column segment.

FIG. 11 illustrates column or implantable malleable penile prosthetic device in accordance with embodiments of the invention.

FIG. 12 illustrates an embodiment of a column segment that includes a slot and a deposit of resilient material.

DETAILED DESCRIPTION OF ILLUSTRATIVE EMBODIMENTS

Figure 1:
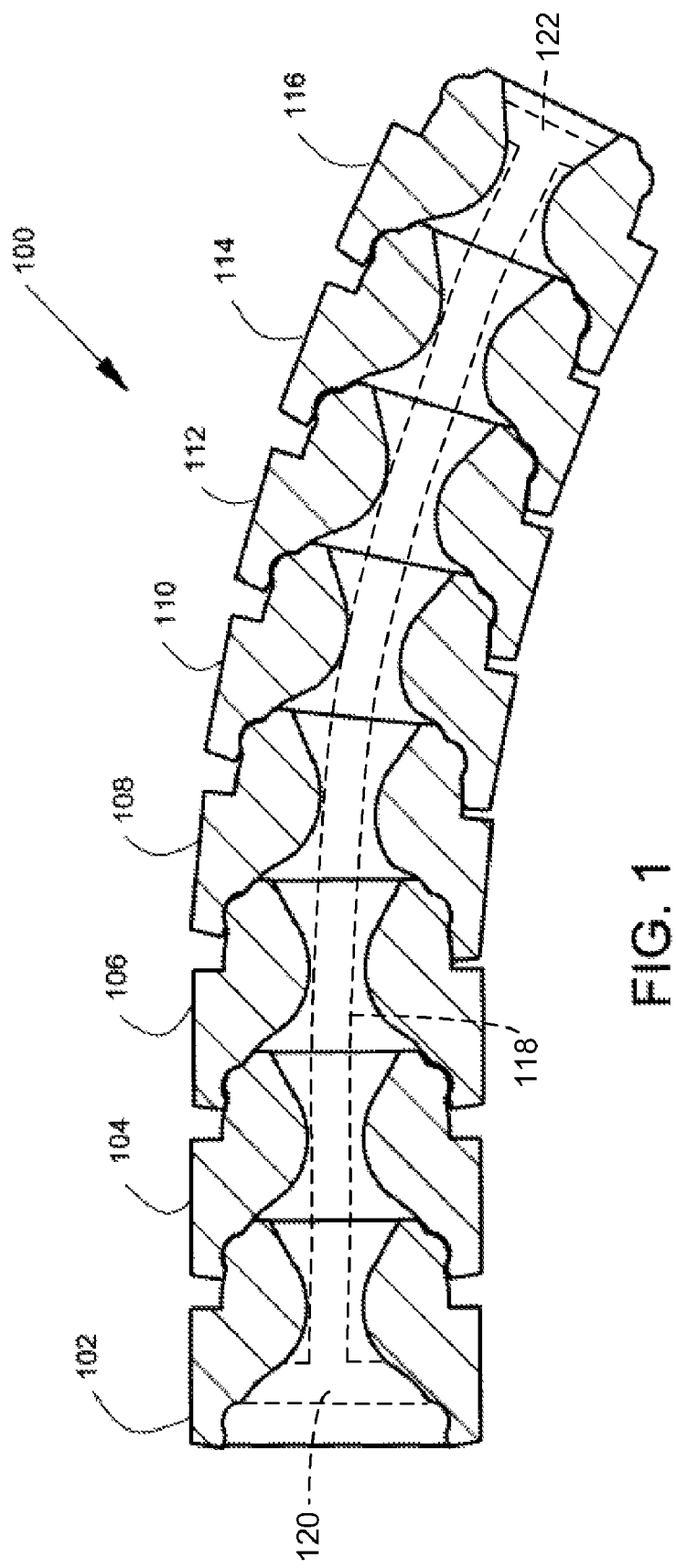
FIG. 1 illustrates column or implantable malleable penile prosthetic device in accordance with embodiments of the invention.

FIG. 1 illustrates a prosthetic device 100, also called a column, in accordance with embodiments of the invention. In one embodiment, the prosthetic device 100 comprises multiple column segments 102, 104, 106, 108, 110, 112, 114, 116 that are stacked as illustrated to form the column 100. An enlarged view of a typical column segment 104 is described in more detail below in connection with FIG. 2.

In one embodiment, the column segments 102-116 are held together with a resilient compression force. In one embodiment, the compressive force is provided by a stretched resilient sleeve that surrounds the column 100. In another embodiment, the resilient compressive force is provided by a stretched member 118 (shown in phantom), such as a spring or cord, for example, that passes through the center of the column 100. The member 118 is secured at either end of the column through the attachment of the member 118 to components 120 and 122 that are recessed within the end column segments 102 and 116 and maintain the member 118 in a stretched state. The column 100 can also include shaped end caps (not illustrated), as needed, to provide desired end shapes to the column 100.

Figure 2:
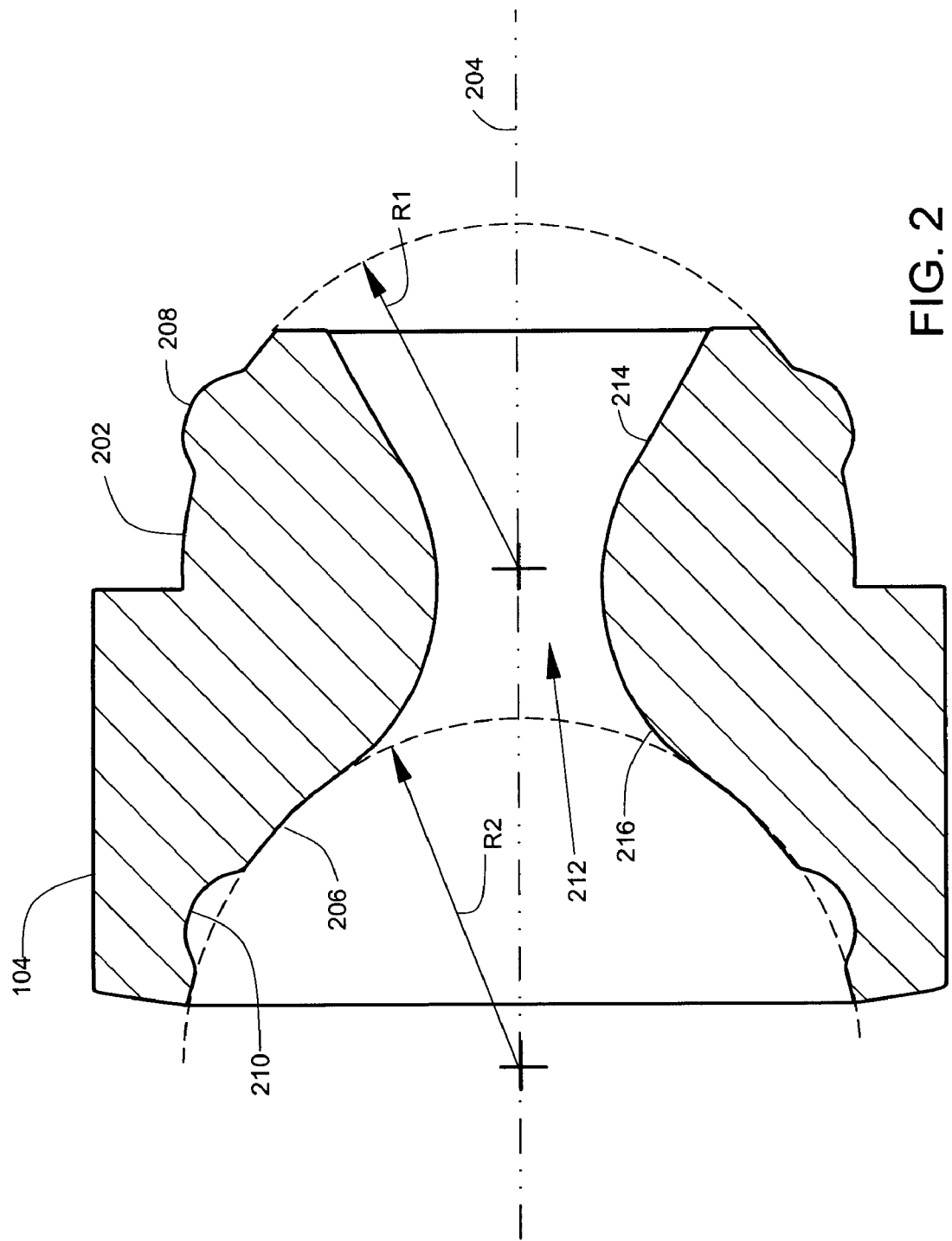
FIG. 2 illustrates an exemplary column segment of the column shown in FIG. 1, in accordance with embodiments of the invention.

As illustrated in FIG. 2, one embodiment of the column segment 104 includes a ball surface 202. In one embodiment, the ball surface 202 comprises a truncated hemispherical portion of a generally spherical surface with a radius R1. The ball surface 202 is generally symmetric about a column axis 204 and faces along the column axis 204 as illustrated. In one embodiment, the ball surface 202 has a generally convex shape. The ball surface 202 is shaped to be articulable in a mating socket of a second one (i.e., column segment 106) of the column segments.

One embodiment of the column segment 104 comprises a socket surface 206 along the column axis 204, facing in a direction opposite that of ball surface 202. One embodiment of the socket surface 206 includes a generally concave shape with a radius R2. The socket surface 206 is articulable on a mating ball of a third one (i.e., column segment 102 in FIG. 2) of the column segments. Radius R2 is selected to be the same as or slightly larger than radius R1 so that mating ball and socket joints fit closely together.

One embodiment of the ball surface 202 includes a protrusion 208. In one embodiment, the protrusion 208 is a generally annular protrusion.

One embodiment of the socket surface 206 includes a recessed portion 210 that is configured to receive or engage the protrusion 208 of the ball surface 202 of a mating column segment (such as column segment 102 in FIG. 1). The engagement with, or reception of, the recessed annular portion 210 with the annular protrusion of the ball surface 202 resists articulation away from a central alignment. Thus, the reception of the protrusion 208 of the column segment 102 within the recessed portion 210 of the column segment 104 stabilizes the column segments 102 and 104 in the central or straight alignment position, in which the axes 204 of the column segments are substantially coaxially aligned with each other. That is, the segments 102 and 104 are resistant to moving out of the straight alignment position, unless acted upon by a sufficient bending force.

One embodiment of the column segment 104 comprises a passageway 212 that extends along the column axis 204. The passageway 212 extends completely through the column segment 104. The passageway 212 permits threading of a slender prosthetic element (such as the stretched member 118 that holds the column together, or tissue elements) along the length of the column 100. In one embodiment, the passageway 212 has outwardly flaring ends 214, 216. The outward flaring of the ends 214, 216 reduces pinching or chaffing of slender prosthetic elements as the column segment 104 is articulated away from column axes of mating column segments.

The shapes of the ball surface 202 and the socket surface 206 and the compressive force on the column tends to align the axis 204 in a straight line with the axes of adjacent mating column segments (such as column segments 102, 106). Once the column 100 is in a straight, central alignment, it tends to stay in a straight central alignment when bending forces are too small to overcome the compressive force, which tends to hold annular protrusions nested in mating annular recesses. The straight central alignment is a first stable alignment state. In FIG. 1, for example, column segments 102, 104, 106 are aligned with one another in the first stable alignment state.

When bending forces increase to a level where the annular protrusion is able to luxate out of the annular recess, however, there is a second, articulated alignment that is bent by a small angle. This second articulated alignment is a second stable alignment state. The alignment of mating column segments can be articulated back and forth between the two stable states by application of a sufficiently large bending force. The column is thus malleable. For a range of smaller bending forces, however, the alignment tends to resist articulation in both stable states. In FIG. 1, for example, column segments 106, 108, 110, 112, 114, 116 are aligned with one another is the second stable alignment state. The small angles of bending between two column segments accumulate over a length of column to bend the column 100 through a larger accumulated angle as illustrated in FIG. 1.

Figure 3:
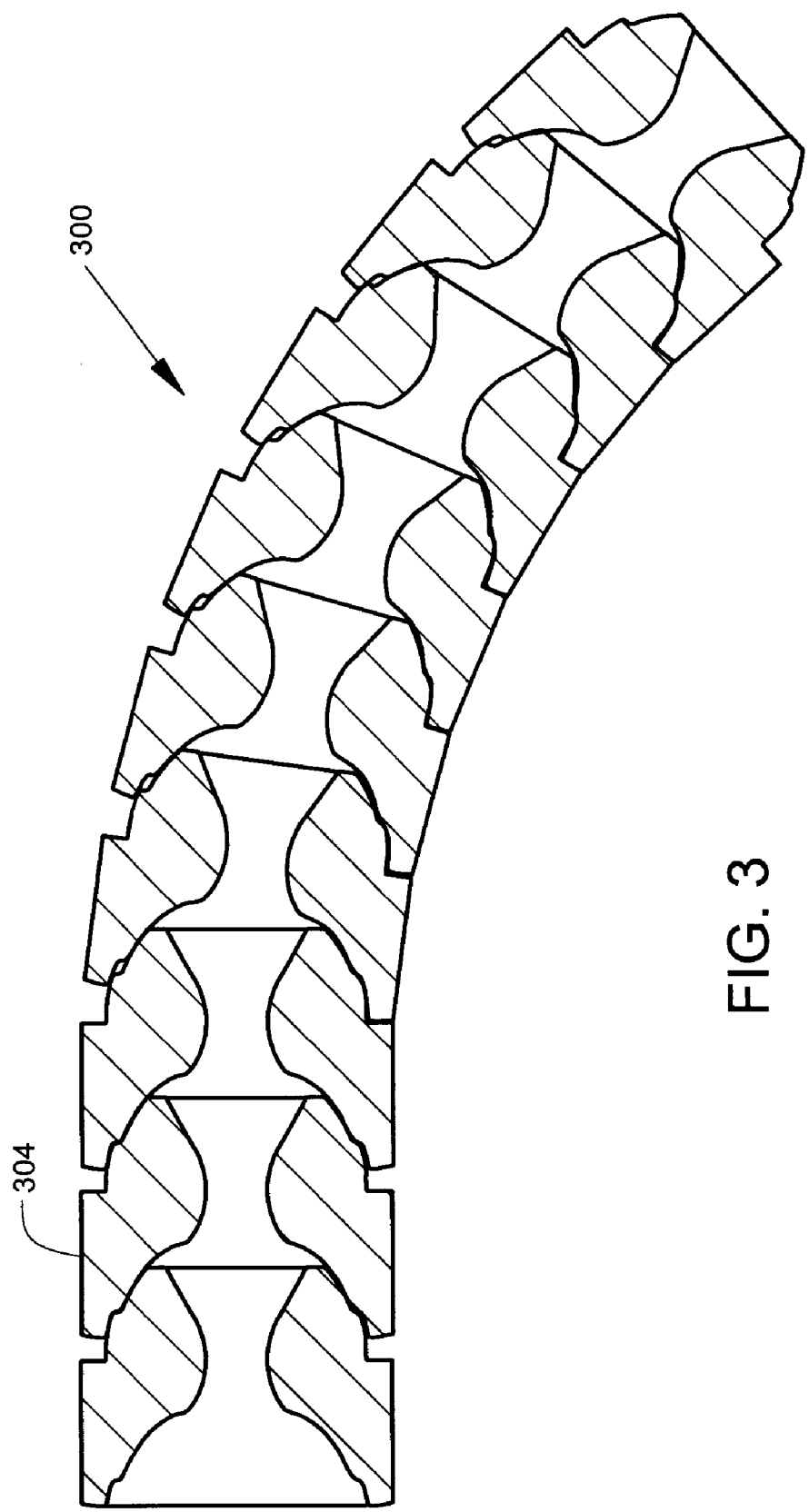
FIG. 3 illustrates column or implantable malleable penile prosthetic device in accordance with embodiments of the invention.
Figure 4:
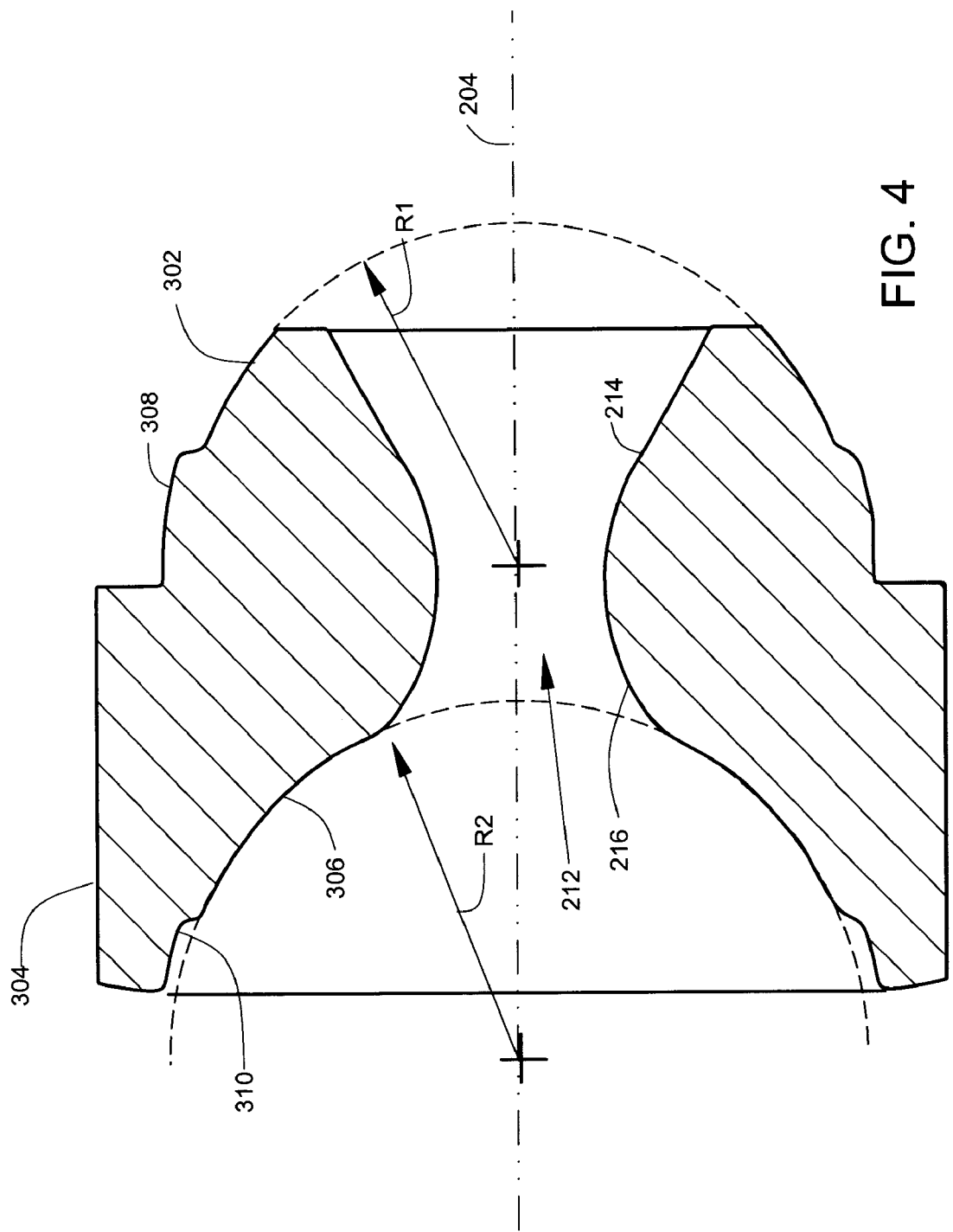
FIG. 4 illustrates an exemplary column segment of the column shown in FIG. 3, in accordance with embodiments of the invention.

FIG. 3 illustrates a column 300 that is formed of multiple column segments such as representative column segment 304. Column 300 is similar to column 100 in FIG. 1 except that the shape of ball and socket surfaces are different. FIG. 4 illustrates the column segment 304. Reference numbers shown in FIG. 4 that are the same as the reference numbers shown in FIG. 2 identify the same or similar features. As illustrated in FIG. 4, embodiments of the column segment 304 include a ball surface 302. One embodiment of the ball surface 302 comprises a truncated hemispherical portion of a generally spherical surface with a radius R1. The ball surface 302 is generally symmetric about a column axis 204 and faces along the column axis 204 as illustrated. The ball surface 302 has a generally convex shape. The ball surface 302 is shaped to be articulable in a mating socket of a mating column segment.

As shown in FIG. 4, one embodiment of the column segment 304 includes a socket surface 306 includes a recessed annular portion 310 that engages an annular protrusion (similar to 308) of a ball surface (similar to 302) of a mating column segment. Alternatively, the surface 310 can be seen as a socket surface and the surface 306 can be seen as an annular protrusion therefrom, while the surface 308 can be seen as a ball surface and the surface 302 can be seen as an annular recess therefrom. The ball and socket shapes illustrated in FIGS. 1-4 are exemplary, however, and other articulable ball and socket shapes can be used as well.

Figure 5:
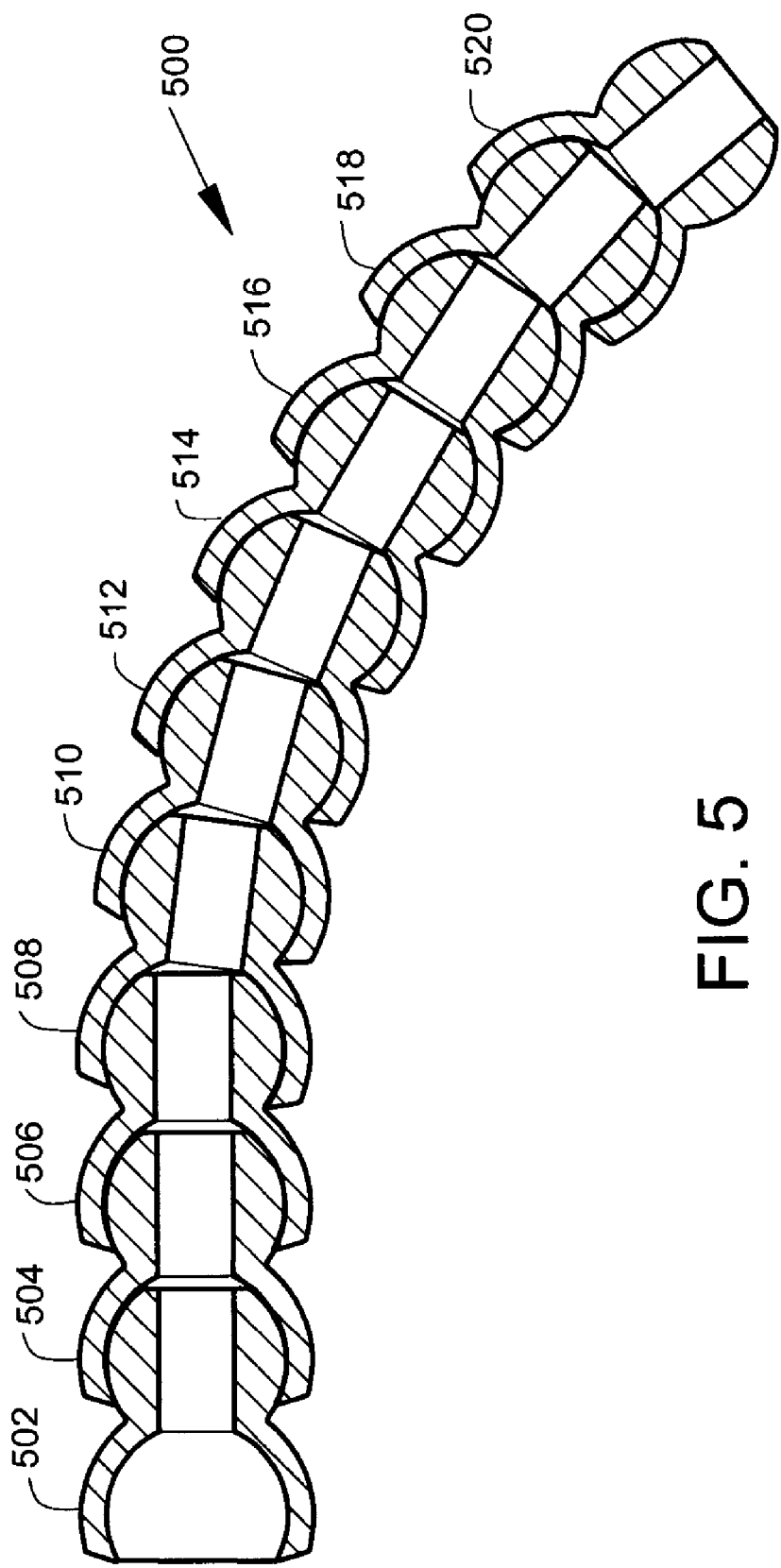
FIG. 5 illustrates column or implantable malleable penile prosthetic device in accordance with embodiments of the invention.

FIG. 5 illustrates a prosthetic device 500, also called a column, in accordance with other embodiments of the invention. The prosthetic device 500 comprises multiple column segments 502, 504, 506, 508, 510, 512, 514, 516, 518, 520 that are snapped together as illustrated to form the column 500. The column segments, such as representative column segment 504, are formed of a material, such as thermoplastic resin, that has an adequate flexibility so that column segments can be forced together as illustrated. The prosthetic device 500 may be assembled at an elevated temperature to increase material flexibility during assembly. Alternatively, column segments may be formed of a material with a high coefficient of thermal expansion such as a metal alloy, and a cold shrunk ball surface may be inserted into a heat expanded socket such that the ball and socket are shrink fit (snapped) together when both ball and socket reach the same temperature. In one process, the metal segments are formed by metal injection molding (MIM), a process that provides net shape parts similar to the net shape process of injection molding of plastics.

In one embodiment, alternative metal segments and plastic segments are used, e.g., column segment 502 comprises metal and column segment 504 comprises plastic. In one embodiment, the mating surfaces between column segment 502 and column segment 504 are textured to increase friction. In another embodiment, a "micro-groove" pattern of ridges and groves are applied in a radial fashion on the ball and socket surfaces. An enlarged view of a representative column segment 504 is described in more detail below in connection with FIG. 6. The column segments 502-520 are held together by ball and socket joints. No external compressive force is needed to hold the column 500 together. The column 500 can also include shaped end caps (not illustrated), as needed, to provide desired end shapes to the column 500.

In one embodiment, a "snap-fit" design element comprises a frictional component between the ball and socket generated by a hoop force (hoop stress) applied by the mechanical design of the socket and the particular material. The amount of hoop force can be adjusted by thickening the wall section, increasing the radial amount of engagement and intentional over sizing of the ball. Reducing the hoop force can be accomplished by adding slots to the socket to allow for easier insertion of the ball.

Figure 6:
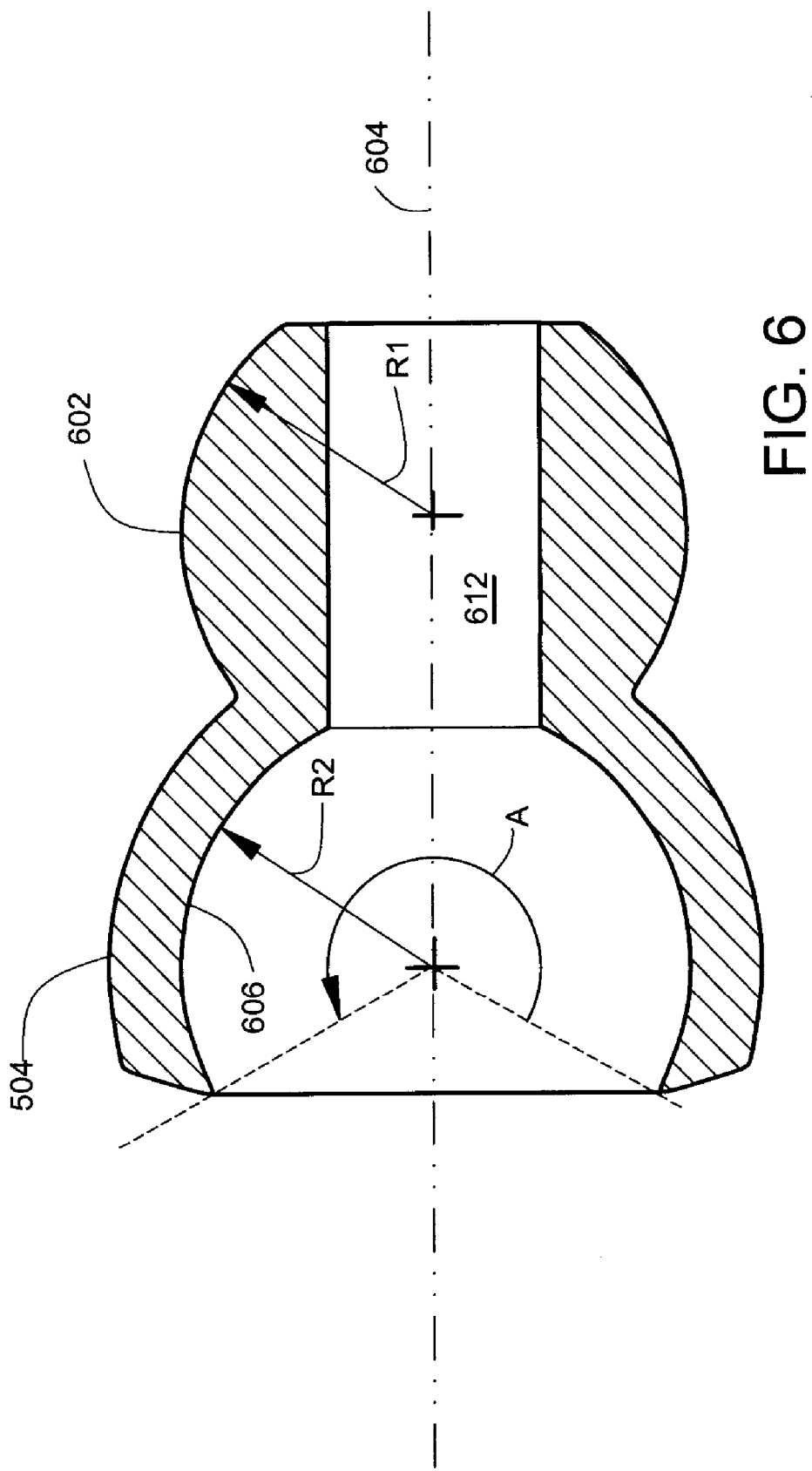
FIG. 6 illustrates an exemplary column segment of the column shown in FIG. 5, in accordance with embodiments of the invention.

As illustrated in FIG. 6, one embodiment of the column segment 504 includes a ball surface 602. In one embodiment, the ball surface 602 comprises a truncated hemispherical portion of a generally spherical surface with a radius R1. The ball surface 602 is generally symmetric about a column axis 604 and faces along the column axis 604 as illustrated. The ball surface 602 has a generally convex shape. The ball surface 602 is shaped to be articulable in a mating socket of a second one (i.e., column segment 606) of the column segments.

One embodiment of the column segment 604 comprises a socket surface 606 along the column axis 604 in a direction opposite that of ball surface 602. The socket surface 606 has a generally concave shape with a radius R2. The socket surface 606 is articulable on a mating ball of a third one (i.e., column segment 602 in FIG. 2) of the column segments. In one embodiment, radius R2 is selected to be the same as or slightly larger than radius R1 so that mating ball and socket joints fit closely together. The socket segment 604 extends along an angle A that is more than 180 degrees to provide a snap or interference fit on the ball surface 602 that strongly resists pulling column segments apart from one another. The opening of the socket extends through an angle of less than 180 degrees, trapping a mating ball segment in the socket segment.

One embodiment of the column segment 504 comprises a passageway 612 that extends along the column axis 604. The passageway 612 extends completely through the column segment 604. The passageway 612 permits threading of a slender prosthetic element (such as a prosthetic tube or tissue elements) along the length of the column 500, for example. The passageway 612 can have outwardly flaring ends (not illustrated) to reduce pinching or chaffing of slender prosthetic elements as the column segment 504 is articulated away from column axes of mating column segments.

Figure 7:
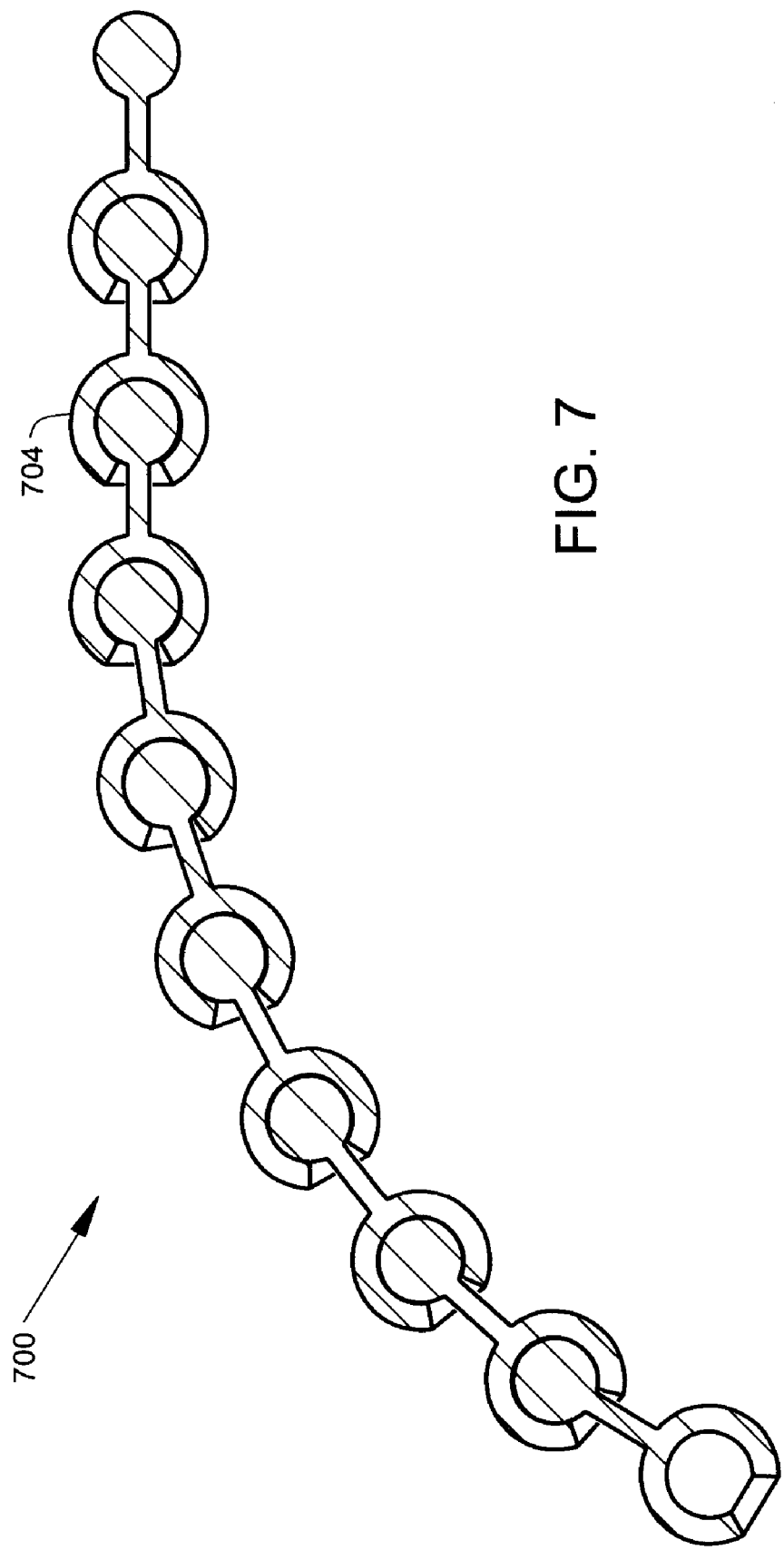
FIG. 7 illustrates column or implantable malleable penile prosthetic device in accordance with embodiments of the invention.
Figure 8:
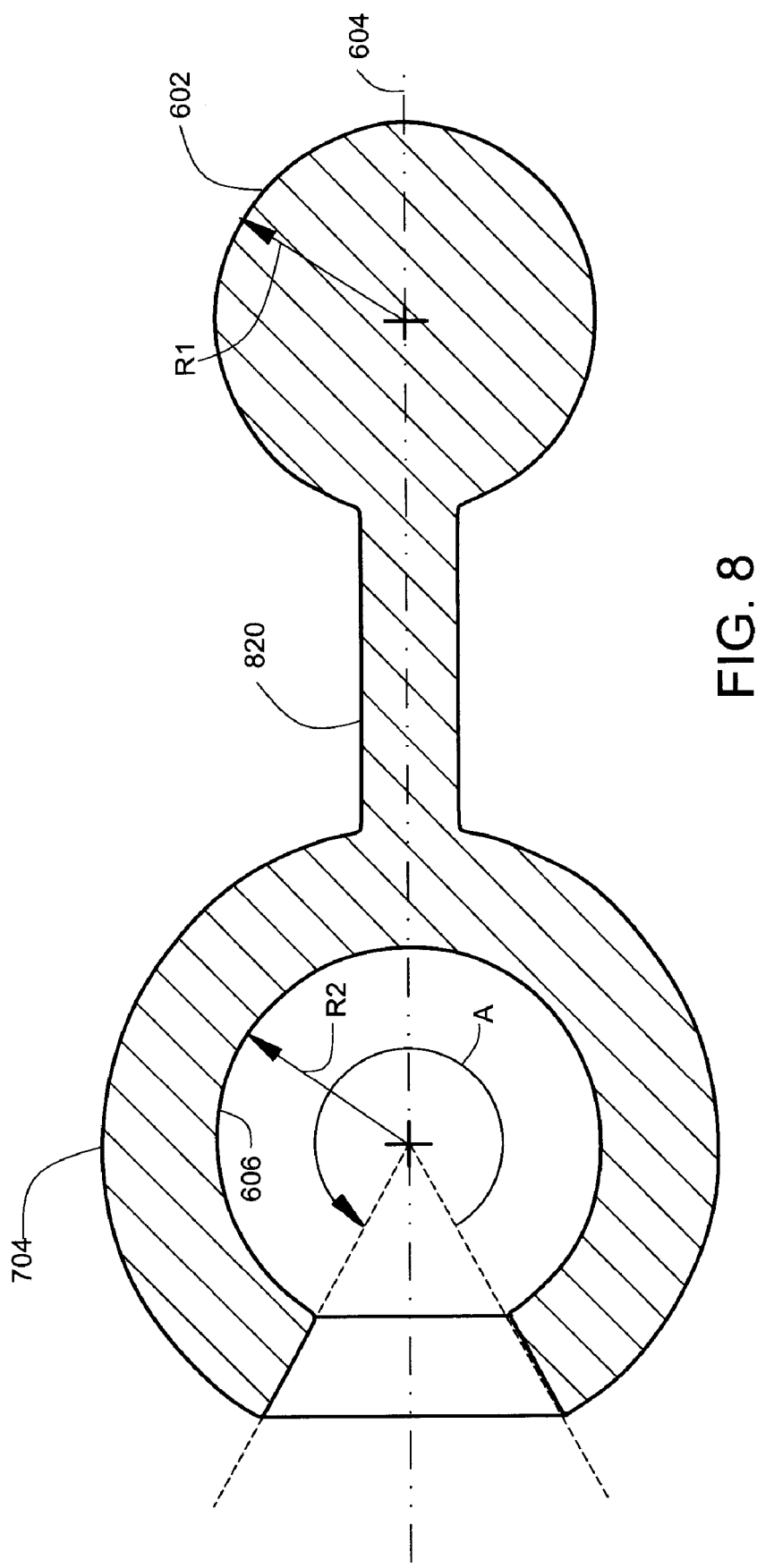
FIG. 8 illustrates an exemplary column segment of the column shown in FIG. 7, in accordance with embodiments of the invention.

FIG. 7 illustrate a column 700 that is formed of multiple column segments such as representative column segment 704. In one embodiment, column 700 is similar to column 500 in FIG. 5 except that ball and socket surfaces are spaced apart and joined by a connecting bar 820 (FIG. 8). In one embodiment, there is no passageway through the column segments. The thin connecting bar 820 permits a wider angle of articulation of the ball and socket joint. FIG. 8 illustrates the representative column segment 704. Reference numbers shown in FIG. 8 that are the same as the reference numbers shown in FIG. 6 identify the same or similar features.

Figure 9:
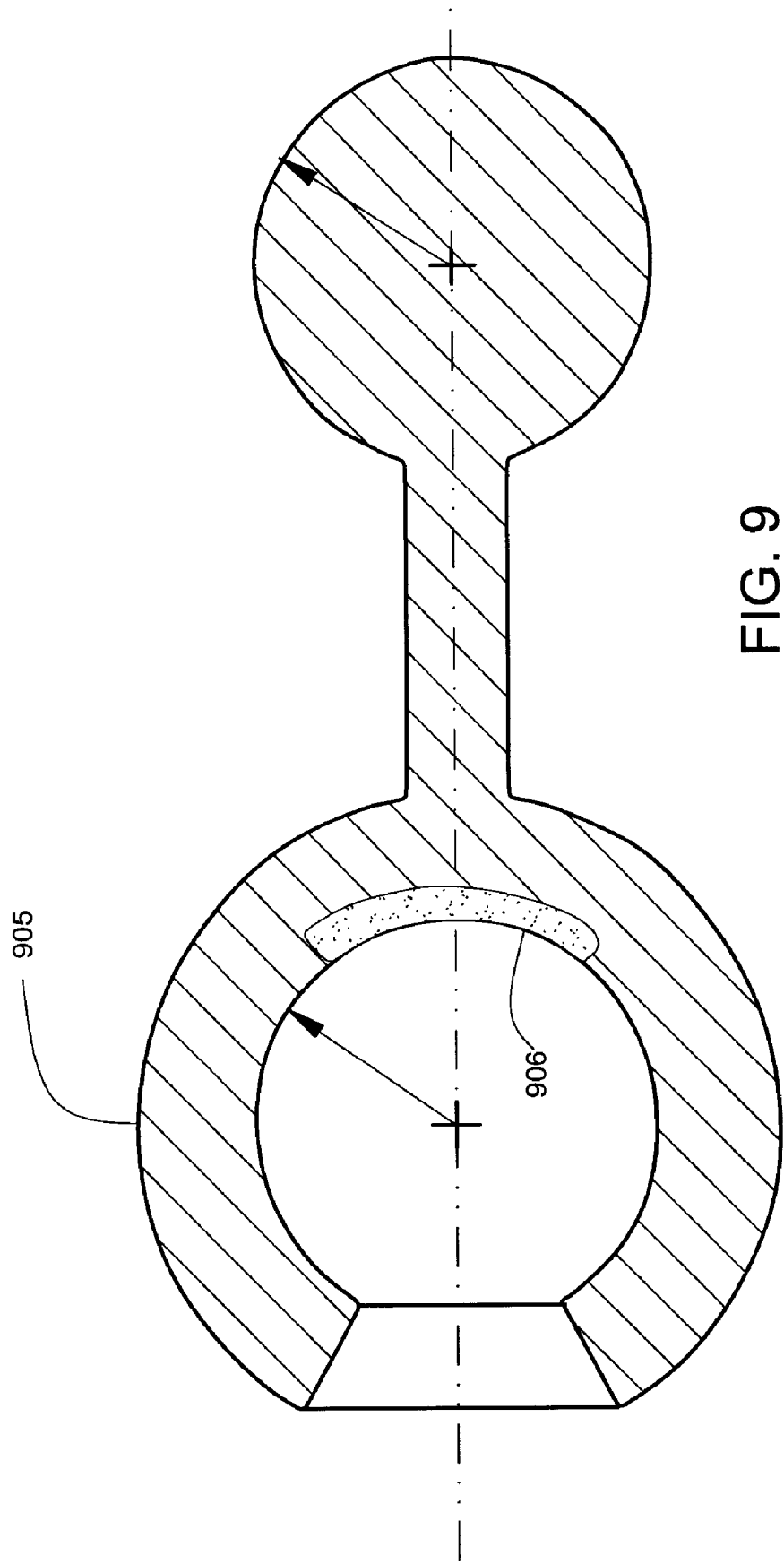
FIG. 9 illustrates an embodiment of a column segment.

FIG. 9 illustrates a column segment 905 that is similar to the column segment 704, except that the column segment 905 includes a friction element 906. In one embodiment, the friction element 906 comprises a deposit of resilient material that is compressed by the mating of ball and socket surfaces. The deposit is deposited in or fills a cavity in the socket surface. The friction element 906 provides increased friction or drag on the articulation motion. The additional drag provides increased resistance to deflection away from a chosen articulated position of the column. The column segment 905 is typically formed of a relatively less resilient thermoplastic material and the deposit is formed a more resilient silicone material or thermoplastic elastomer. Friction element 906 is under compression from the mating ball section. This configuration increases the friction between the mating elements. The materials of the deposit are selected on their compression characteristic noted as durometer and their coefficient of friction. The shape of the deposit that is shown in exemplary, and other deposit shapes can be used as well. The shape of column segment 904 is exemplary, and other column segment shapes can be used with deposits of resilient material as well.

In one embodiment, the friction element 906 comprises, instead of a silicone or thermoplastic deposit, a compression spring washer ("Belleville washer"), a coiled compression spring or a leaf spring. The friction element 906 is envisioned to be placed in one or multiple locations within the socket and or ball circumference.

FIG. 10A illustrates a cross-sectional side view, FIG. 10B illustrates an end view, and FIG. 10C illustrates a top view of a column segment 1004 in accordance with embodiments of the invention. Column segment 1004 is similar to column segment 704 in FIG. 8, except that column segment 1004 includes a slot 1006 that is formed in a socket portion of the column segment. The slot 1006 permits a wider angle of articulation in the direction of the slot 1006, while maintaining a narrower angle of articulation for other directions of articulation. A connecting bar (shaped like connecting bar 1020) of a mating column segment is able to move in the slot 1006 along a wide angle.

FIG. 11 illustrates a column 1100 which includes representative column segment 1004 with slot 1006. As illustrated, a wide angle of articulation B is obtained with use of the slot 1006.

FIG. 12 illustrates a column segment 1104 which is similar to column segment 1004 except that column segment 1104 includes deposits 1022, 1024 of resilient material. Reference numbers used in FIG. 12 that are the same as reference numbers used in FIG. 10 identify the same or similar features. The deposits 1022 or 1024 are compressed when the articulation in the slot reaches it maximum allowable angle. The deposits 1022, 1024 function as resilient bumpers or snubbers to provide a cushioning effect as the articulation reaches its maximum limit in the slot.

Figure 13:
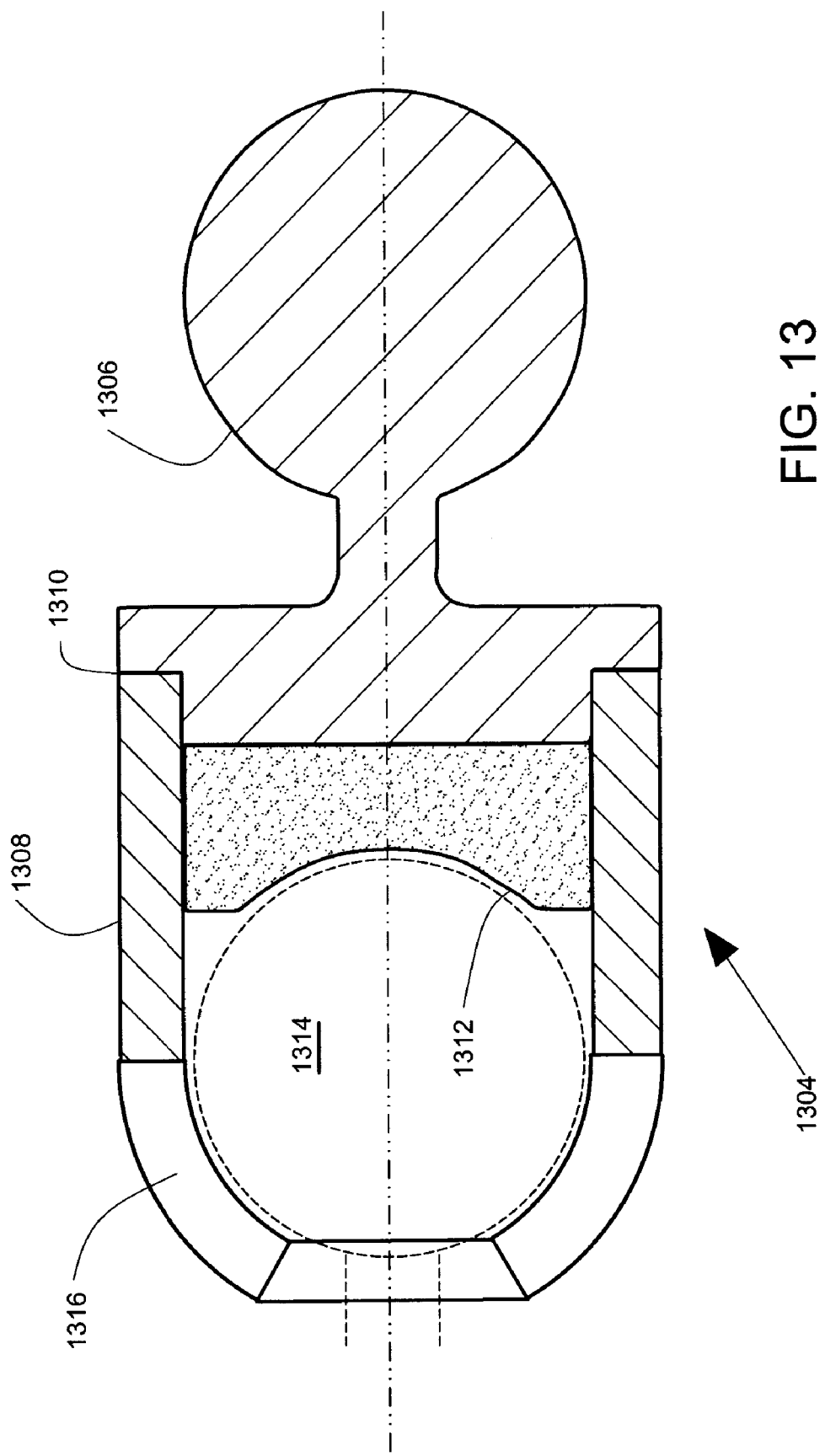
FIG. 13 illustrates an embodiment of a column segment.

FIG. 13 illustrates an alternative embodiment of a column segment 1304. The column segment 1304 includes a ball portion 1306 and a socket portion 1308 that are assembled and welded at seam 1310. Seam 1310 is preferably welded using ultrasonic welding or solvent welding. A deposit 1312 of resilient material is provide inside a socket 1314. The deposit 1312 can function as a frictional element for rotation of a mating ball inside the socket 1314 and also as a snubber for axial impact. It will be understood from FIG. 13 that a mating ball is inserted in socket 1314 before the joint 1310 is welded. The socket portion 1308 includes a slot 1316 to provide an increase range of articulation in a direction along the slot 1316.

Figure 14:
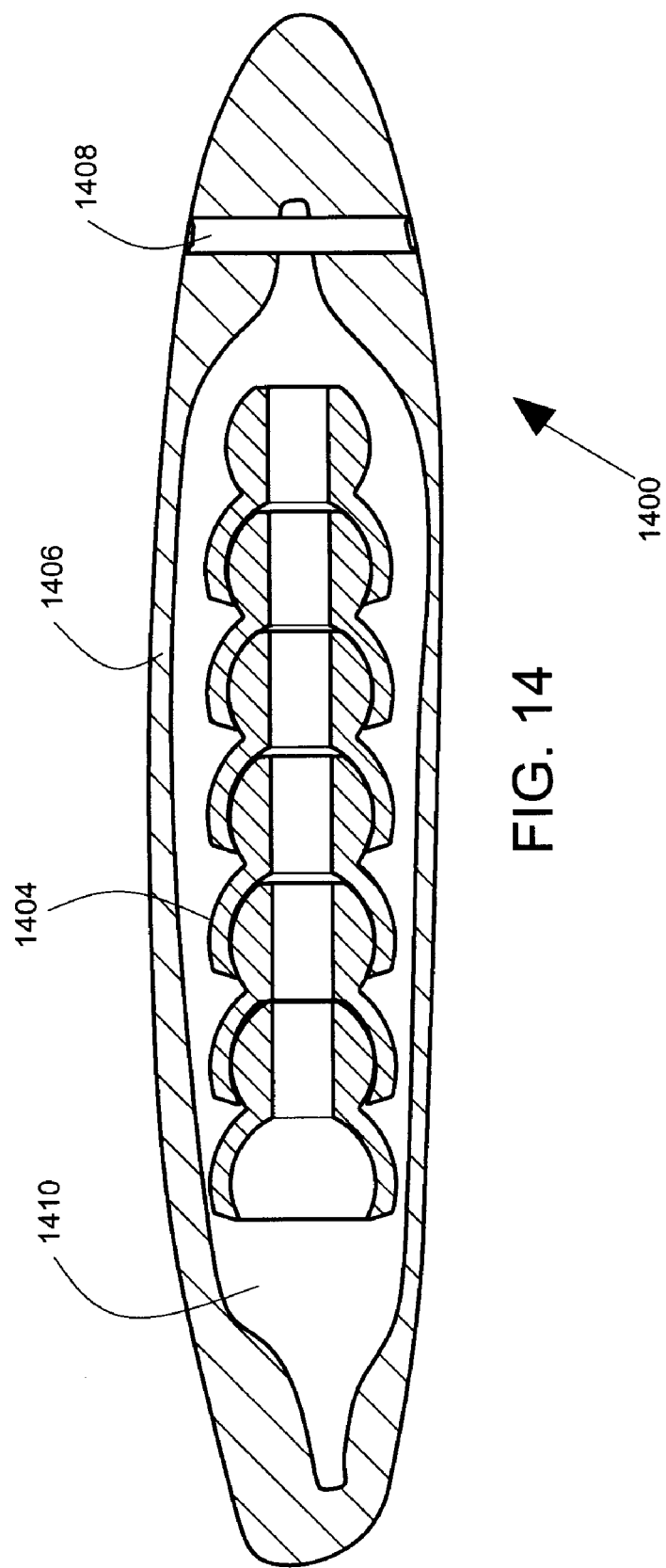
FIG. 14 illustrates an implantable malleable penile prosthetic device in accordance with embodiments of the invention.

FIG. 14 illustrates an exemplary malleable penile prosthesis 1400, in accordance with embodiments of the invention, that includes a column 1404 formed of exemplary column segments. The column 1404 is formed of column segments such as those described above in connection with FIGS. 1-13. The column 1404 is embedded in a body 1410 of resilient material that can include a lubricant for the column segments. In one embodiment, a centering disc 1008 centers the body 1410 with respect to an outer sheath 1406 which contains the body 1410 and the lubricant.

Figure 15:
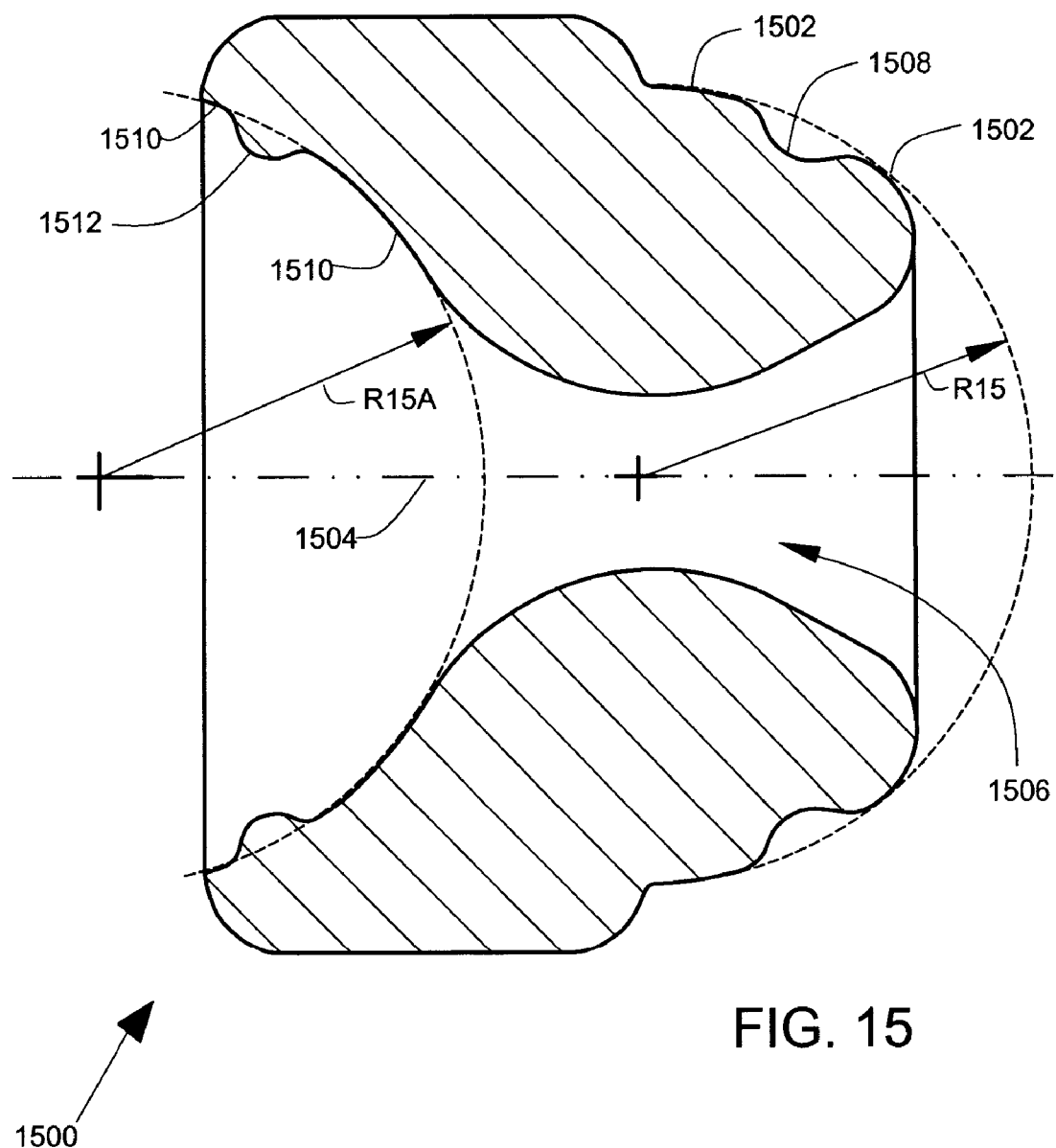
FIG. 15 illustrates an embodiment of a column segment.

FIG. 15 illustrates an embodiment of a column segment 1500. The column segment 1500 includes a ball surface 1502. The ball surface 1502 comprises portions of a generally spherical surface with a radius R15. The ball surface 1502 is generally symmetric about a column axis 1504 and faces along the column axis 1504 as illustrated. The ball surface 1502 has a generally convex shape that is interrupted by an annular groove 1508 and that is interrupted by an opening 1506. The ball surface 1502 is shaped to be articulable in a mating socket of a mating column segment.

A socket surface 1510 comprises portions of a generally spherical surface with radius R15A. The socket surface 1510 includes a protruding annular portion 1512 that engages an annular protrusion (similar to 1508) of a ball surface (similar to 1502) of a mating column segment.

In one embodiment, the spherical convex radius R15 is about 0.140 inch, the spherical concave radius R15A is about 0.142 inch, and the outer diameter of the column segment 1500 is about 0.33 inches. In one embodiment, the column segment 1500 comprises polyethylene. In one embodiment, the center-to-center spacing along the axis 1504 between the socket surface 1510 and the ball surface 1502 is 0.20 inch.

Figure 16:
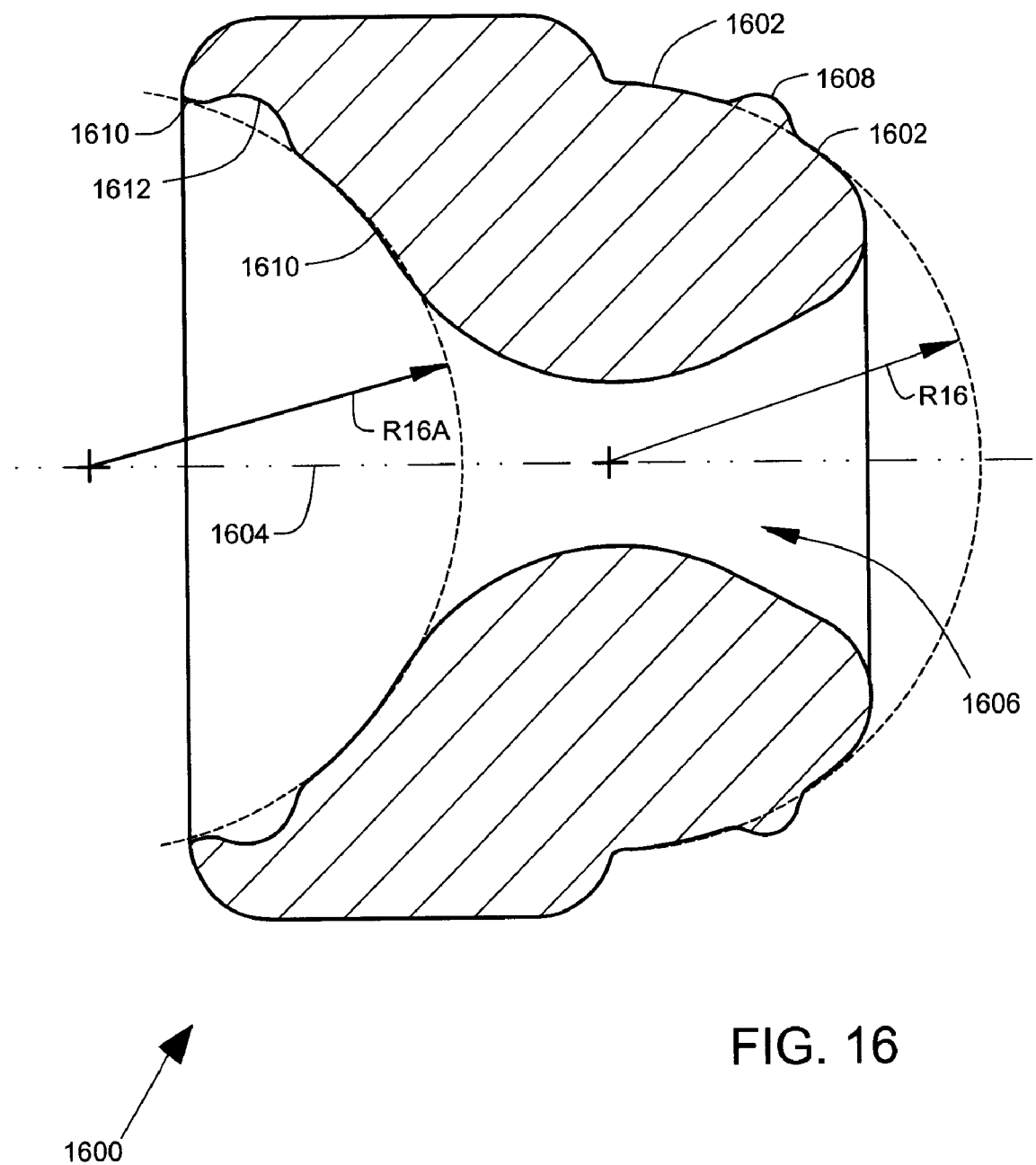
FIG. 16 illustrates an embodiment of a column segment.

FIG. 16 illustrates an embodiment of a column segment 1600. The column segment 1600 includes a ball surface 1602. The ball surface 1602 comprises portions of a generally spherical surface with a radius R16. The ball surface 1602 is generally symmetric about a column axis 1604 and faces along the column axis 1604 as illustrated. The ball surface 1602 has a generally convex shape that is interrupted by an annular protrusion 1608 and that is interrupted by an opening 1606. The ball surface 1602 is shaped to be articulable in a mating socket of a mating column segment.

A socket surface 1610 comprises portions of a generally spherical surface with radius R16A. The socket surface 1610 includes a grooved or recessed annular portion 1612 that engages an annular protrusion (similar to 1608) of a ball surface (similar to 1602) of a mating column segment.

In one embodiment, the spherical convex radius R16 is about 0.140 inch, the spherical concave radius R16A is about 0.142 inch, and the outer diameter of the column segment 1600 is about 0.33 inches. In one embodiment, the column segment 1600 comprises polyethylene. In one embodiment, the center-to-center spacing between the socket surface 1610 and the ball surface 1602 is 0.20 inch.

In the embodiments described above, the rigidity of the prosthetic device is improved without sacrificing concealment.

In the embodiments shown in FIGS. 1-4, the column segments lock or provide increased resistance to deflection away from a straight axial alignment. The increased resistance is noticeable only the approximately straight position. The increased resistance in the straight position increases device rigidity in the straight position. It is easier to straighten the column into straight axial alignment for use. Embodiments can include rings, grooves, radius or knobs to provide locking.

A column for a low cost implantable, non-inflatable penile prosthetic device is provided. The column forms a center flexible core of the penile prosthesis that can be made of biocompatible plastic resin column segments that fit together. The column segments can snap together or be held together by a spring that is either external or internal to the column, the ball end of one column segment fits into the socket end of the next column segment. The friction needed for column strength come from the fit of the column segments. The fit can be an interference fit. The flexibility or articulability of the column come from rotation of ball and socket surfaces relative to one another. The column has flexibility and concealability comparable to existing prosthetic devices, but with far fewer components and less assembly time. The device also has potential for greater column strength than existing devices. With a snap together embodiment, there are no springs and wires to rub and make noises that are characteristic of existing designs. With few moving parts and no cable crimps, there is little opportunity for mechanical failure of the column. A silicone outer body can be provided to enclose the column. A flexible hose segment can pass through the center of the column components can be machined or injection molded from thermoplastic materials. The curvature of the device is limited by the interference of the segments as the column flexes. The outside diameter of one segment fits the inside diameter of the next segment. Each joint between segments has a small amount of articulation. The combined articulation provides total articulation that is comparable to existing devices. A malleable body can be pulled over the column and bonded in place. Joints between column segments can be lubricated with fluorosilicone. Column segments can snap together with interference fit. The interference fit provide column strength. Column ends with convention outer end shapes can include ball or socket features to fit or snap on the ends of the column.

Embodiments that include ball and socket surfaces that snap together do not require the use cables or springs to hold the column together, making the column easier to manufacture and less costly. Compressive material can be used for increased ball to socket friction, holding strength and rigidity. Increased degrees of rotation in a selected direction can be provided by providing a slot in a column segment. Compressible polymers such as silicone can be used. More complex components can be formed of smaller parts are joined by ultrasonic welding or other known joining methods. The use of column segments to form a column provides a modular design in which the length of the column can be adjusted by assembling a selected number of column segments to match the needs of a particular patient.

Although the present invention has been described with reference to preferred embodiments, workers skilled in the art will recognize that changes may be made in form and detail without departing from the spirit and scope of the invention.

What is claimed is:

1. An implantable malleable penile prosthetic device, comprising:
   a stack of column segments, comprising:
      a first column segment comprising a first column axis and a ball surface having a generally convex shape facing along the first column axis and a socket surface having a generally concave shape facing in an opposite direction along the first column axis;
      a second column segment comprising a second column axis and a mating socket, wherein the ball surface of the first column segment is articulable in the matting socket of the second column segment; and
      a third column segment comprising a third column axis and a mating ball, wherein the socket surface of the first column segment is articulable on the mating ball of the third column segment;
   wherein:
      the ball surface of the first column segment includes a protrusion that engages a portion of the mating socket of the second column segment to resist articulation away from a central alignment of the first and second column axes, or
      the socket surface of the first column segment includes a protrusion that engages a portion of the mating ball of the third column segment to resist articulation away from a central alignment of the first and third column axes.

2. The prosthetic device of claim 1, wherein the first column segment comprises a passageway extending along the first column axis.

3. The prosthetic device of claim 2 further comprising a stretched member extending through the passageway of the first column segment.

4. The prosthetic device of claim 1, wherein the ball surface of the first column segment is substantially spherical.

5. The prosthetic device of claim 1, wherein the socket surface of the first column segment is substantially spherical and comprises a pivoting slot that is generally parallel with the first column axis.

6. The prosthetic device of claim 1 further comprising a deposit of resilient material disposed on the first one of the column segments, the resilient material being compressed by articulation.

7. The prosthetic device of claim 1, wherein the ball surface of the first column segment snaps into the mating socket of the second column segment and the socket surface of the first column segment snaps over the mating ball of the third column segment to resist pulling the first, second and third column segments apart.

8. The prosthetic device of claim 1 further comprising an interference fit between the ball surface of the first column segment and the mating socket of the second column segment.

9. An implantable malleable penile prosthetic device, comprising:
- a first column segment comprising a first column axis and a socket surface facing along the first column axis, the socket surface having a generally concave shape;
- a second column segment comprising a second column axis and a ball surface facing along the second column axis, the ball surface having a generally convex shape that is articulable in the socket of the first column segment; and a socket surface facing an opposite direction along the second column axis; and
- a third column segment comprising a third column axis and a ball surface facing along the third column axis, the ball surface having a generally convex shape that is articulable in the socket of the second column segment;

wherein:
- the first and second column segments comprise:
  - a first alignment state, in which the first and second column axes are substantially coaxially aligned; and
  - a second alignment state, in which the first and second column axes are not coaxially aligned;
- an annular protrusion is formed in one of the socket surface of the first column segment and the ball surface of the second column segment, and an annular recessed portion is formed in the other of the socket surface of the first column segment and the ball surface of the second column segment;
- the first and second column segments are stabilized in the first alignment state when the protrusion is received within the recessed portion.

10. The prosthetic device of claim 9, further comprising a sheath surrounding the first, second and third column segments.

11. The prosthetic device of claim 9, wherein:
- the first column segment comprises a passageway extending along the first column axis;
- the second column segment comprises a passageway extending along the second column axis;
- the third column segment comprises a passageway extending along the third column axis; and
- the prosthetic further comprises a stretched member extending through the passageways of the first, second and third column segments, wherein the stretched member compresses the first, second and third column segments together.

12. An implantable malleable penile prosthetic device, comprising:
- a first column segment comprising a fist column axis and a socket surface facing along the first column axis, the socket surface having a generally concave shape and including a pivoting slot that is generally parallel with the first column axis; and
- a second column segment comprising a second column axis a ball surface facing along the second column axis, the ball surface having a generally convex shape that is articulable in the socket of the first column segment, a socket surface facing an opposite direction along the second column axis and a bar connecting the ball surface to the socket surface.

13. The prosthetic device of claim 12, wherein:
the first and second column segments comprise a straight position in which the first and second column axes are substantially coaxial; and
a bent position in which the bar is received within the slot of the socket surface of the first column segment and the column axes are non-coaxial.

14. The prosthetic device of claim 13, wherein the socket surfaces are substantially spherical and the ball surface is substantially spherical.

15. The prosthetic device of claim 14, wherein the ball surface snaps into the socket surface of the first column segment to resist pulling the first and second column segments apart.

* * * * *